United States Patent [19]
Zukowski

[11] Patent Number: 5,462,781
[45] Date of Patent: Oct. 31, 1995

[54] SURFACE MODIFIED POROUS EXPANDED POLYTETRAFLUOROETHYLENE AND PROCESS FOR MAKING

[75] Inventor: Stanislaw L. Zukowski, Flagstaff, Ariz.

[73] Assignee: W. L. Gore & Associates, Inc., Newark, Del.

[21] Appl. No.: 236,305

[22] Filed: May 2, 1994

Related U.S. Application Data

[63] Continuation-in-part of Ser. No. 161,184, Dec. 1, 1993, which is a continuation of Ser. No. 718,324, Jun. 14, 1991, abandoned.

[51] Int. Cl.$^6$ ............... A61F 2/01; A61F 2/04; A61F 2/06; A61F 2/52; A61L 27/00; B32B 33/00
[52] U.S. Cl. ............... 428/36.1; 128/DIG. 14; 216/58; 216/67; 204/157.61; 204/157.63; 204/192.11; 204/192.36; 427/534; 427/551; 427/554; 427/569; 428/36.4; 428/36.9; 428/36.92; 428/224; 428/308.4; 428/311.5; 428/376; 428/398; 428/409; 428/422; 600/36; 606/231; 623/1; 623/8; 623/11; 623/12; 623/66; 623/901
[58] Field of Search .............. 128/DIG. 14; 156/643; 204/157.61; 427/534, 569; 428/36.1, 36.4, 36.9, 36.92, 224, 308.4, 311.5, 376, 398, 409, 422; 600/36; 606/231; 623/1, 8, 11, 12, 66, 901

[56] References Cited

U.S. PATENT DOCUMENTS 4,187,390  2/1980  Gore .................... 428/324

OTHER PUBLICATIONS

Morra et al, *Langmuir*, 1989; 5; 872–876.

Primary Examiner—James C. Cannon
Attorney, Agent, or Firm—Wayne D. House

[57] ABSTRACT

An implantable porous expanded polytetrafluoroethylene material having a microstructure of nodes interconnected by fibrils wherein a surface of the material has been modified by the removal of fibrils from the surface so that under magnification the surface has the appearance of freestanding node portions not interconnected by fibrils but rather having open valleys disposed between the freestanding node portions. Unmodified material beneath the surface maintains the original microstructure of nodes interconnected by fibrils. The modification is preferably done by exposing the surface to radio frequency gas plasma discharge with a reactive etching gas for a lengthy amount of time such as about ten minutes. The depth of fibril removal from the surface is substantially a function of the duration and amount of energy applied to the surface.

17 Claims, 12 Drawing Sheets

SURFACE MODIFIED POROUS EXPANDED POLYTETRAFLUOROETHYLENE AND PROCESS FOR MAKING

CROSS-REFERENCE TO RELATED APPLICATION

This application is a continuation-in-part of application Ser. No. 08/161,184 filed Dec. 1, 1993 which is a continuation of application Ser. No. 07/718,324 filed on Jun. 14, 1991, now abandoned.

FIELD OF THE INVENTION

This invention relates to surface modified porous expanded polytetrafluoroethylene and a method for making it.

BACKGROUND OF THE INVENTION

It has long been known to use various surface modification techniques including glow discharge plasma to change the surface characteristics of polymeric materials. For example, it may be advantageous to improve the bondability of an implantable polymeric medical device or to change the wettability of a polymeric fabric. Fluorocarbons have frequently been used as both the surface modified substrate materials and as materials used to modify surfaces of other polymeric substrates.

These surface modifications can take several forms. Plasma polymerization by radio frequency gas plasma using polymerizing gases can polymerize a new material onto the surface of another substrate. Unsaturated fluorocarbon gas plasmas can be used, for example, to polymerize a fluorocarbon layer onto a polystyrene substrate. Alternatively, plasma activation is used with non-polymer forming gases such as oxygen or saturated fluorocarbons to chemically modify a substrate surface. The plasma activation of a fluoropolymer substrate surface with oxygen gas, for example, can result in the replacement of fluorine atoms from the substrate surface with oxygen in order to enhance the wettability of that surface. Still another technique is plasma cleaning or plasma etching where a reactive gas plasma is used to etch or roughen a surface by removing quantities of the substrate material comprising the surface. This can be done for surface cleaning or for increasing bondability, for example. Etching can also be accomplished with other energy sources such as ion beams. Masking techniques can be used to selectively etch portions of a surface to produce a desired pattern. Alternatively, specific surface patterns can be produced in polymeric surfaces by molding techniques well known to those skilled in the art.

Plasma polymerization, plasma activation and plasma etching are all considered to be specific types of plasma treatment but are not considered as mutually exclusive categories. The plasma etching of some substrates to enhance bondability is, for example, sometimes called plasma activation.

An article in Medical Product Manufacturing News (Using Gas Plasma to Re-engineer Surfaces, Nancy B. Mateo, September/October 1990), provides a general description of known gas plasma surface modification methods. The author states that increasing surface wettability and adhesiveness are among the most routine uses for gas plasmas.

U.S. Pat. No. 4,919,659 to Horbett, et al., teaches the modification of bio-material surfaces by radio frequency plasma in order to enhance the growth of cell cultures on the bio-material surfaces. The modification involves the plasma polymerization of overcoat layers onto a surface of an implantable bio-material.

A paper by A. M. Garfinkle et al., ("Improved Patency in Small Diameter Dacron Vascular Grafts After a Tetrafluoroethylene Glow Discharge Treatment," presented at the Second World Congress on Biomaterials 10th Annual Meeting of the Society for Biomaterials, Washington, D.C., Apr. 27–May 1, 1984) describes the use of plasma polymerization with the monomer TFE gas to modify the luminal surface of Dacron vascular grafts by depositing thereon a coating of tetrafluoroethylene.

An article by C. Tran and D. Walt (Plasma Modification and Collagen Binding to PTFE Grafts. Journal of Colloid and Interface Science, Oct. 15, 1989, vol 132 no. 2, pp 373–381), describes the use of RF and electrical glow discharge plasma deposition systems to clean and coat the luminal surface of porous expanded polytetrafluoroethylene GORE-TEX® Vascular Grafts. Cleaning was done with argon plasma for one hour followed consecutively by plasma polymerization with hexane and anhydrous ammonia for one hour each. The grafts were then coated with collagen. Wettability of the plasma modified polytetrafluoroethylene (hereinafter PTFE) surface was found to be increased. Y. S. Yeh et al. (Blood Compatibility of Surfaces Modified by Plasma Polymerization. Journal of Biomedical Materials Research 1988 22;795–818) used rf gas plasma in a hexafluoroethane/$H_2$ atmosphere to polymerize the surface of GORE-TEX Vascular Grafts. They described the surface morphology of the treated graft surfaces as being indistinguishable from untreated graft surfaces.

Y. Iriyama et al. (Plasma Surface Treatment on Nylon Fabrics by Fluorocarbon Compounds. Journal of Applied Polymer Science 1990 39;249–264) plasma polymerized or alternatively plasma activated nylon fabrics with low temperature fluorocarbon plasmas so as to increase the hydrophobicity of these fabrics. They found water droplet roll-off angle to be a better indicator of rough surface hydrophobicity than measurements of water droplet contact angles. A good description of the method of making water droplet roll-off angle measurements is provided.

In U.S. Pat. No. 4,946,903, J. Gardella et al., teach plasma activation of fluoropolymers with radio frequency glow discharge to increase the wettability of their surfaces. This is accomplished by substituting hydrogen and oxygen or oxygen-containing radicals for fluorine atoms in the surface of the fluoropolymer. Porous expanded PTFE was used as an example fluoropolymer.

M. Morra et al., (Contact Angle Hysteresis in Oxygen Plasma Treated Polytetrafluoroethylene, Langmuir 1989 5;872–876; Surface Characterization of Plasma-Treated PTFE, Surface and Interface Analysis 1990 16;412–417), exposed non-porous PTFE surfaces to both oxygen and argon gas plasmas. With oxygen plasmas they found that 15 minute treatments produced extensive plasma etching of the surface while argon treatment for the same time did not alter surface smoothness. The argon treated surfaces were found to be more hydrophilic than the untreated precursor material. Morra also described that the roughened surface resulting from oxygen plasma treatment showed increased hydrophobicity as a direct function of the increased surface roughness, with water advancing contact angles up to 166 degrees.

U.S. Pat. No. 4,933,060 to Prohaska, et al., teaches the plasma modification of a fluoropolymer surface by treatment with reactive gas plasma comprising primarily water, in order to increase the adhesive bondability of such surfaces. The surfaces are rendered hydrophilic, apparently by the defluorination and oxidation of the surface.

U.S. Pat. No. 4,064,030 to J. Nakai et al., describes the modification of molded non-porous articles of fluorine resin by sputter etching with ion beams in order to provide better adhesion. They state that their treated surfaces have superior adhering properties not attainable with conventional glow discharge treatment. Nakai et al., noted that wettability of a surface can be modified by varying treatment time, discharge power or chamber pressure, however no modified surfaces were described as being more hydrophobic than untreated PTFE having contact angles up to about 120 degrees.

An article by S. R. Taylor, et al., "Effect of Surface Texture On The Soft Tissue Response To Polymer Implants," Journal of Biomedical Materials Research 1983 17;205–227, John Wiley & Sons, Inc., describes ion beam etching by sputtering of non-porous PTFE surfaces. A modified textured PTFE surface having conical projections was produced wherein the projections had a mean height of about 12 microns, a mean base width of about 4 microns and a mean tip radius of about 0.1 micron. Little or no apparent chemical changes in the modified surface were detected. When implanted in a living body, these modified PTFE surfaces produced fibrous capsules of only 30 percent of the thickness of fibrous capsules produced by unmodified PTFE surfaces. The modified surfaces also demonstrated increased cell adhesion. Contact angle measurements were used to determine the surface energy of the modified PTFE surfaces, however, no results of surface energy analysis and no contact angle data were provided for the modified textured PTFE surfaces because of wicking of the diagnostic liquids on those surfaces.

G. L. Picha et al., ("Ion-Beam Microtexturing of Biomaterials," Medical Device and Diagnostic Industry, vol. 6 no. 4, April 1984), describe the manufacture of textured surfaces in non-porous PTFE and polyurethane by etching surfaces with ion-beams, with and without the optional use of sputter masks, for the purpose of increasing bondability.

U.S. Pat. No. 4,955,909 to Ersek et al., describes textured silicone surfaces for implantable materials wherein the surfaces comprise a series of formed pillars with valleys disposed between them. The textured surface is produced by thrusting specifically selected molecules against a non-porous silicone rubber surface with sufficient impact to produce pillars or projections of 20 to 500 micron size.

U.S. Pat. Nos. 4,767,418 and 4,869,714 to Deininger et al., describe a male mold useful for making tubular vascular grafts, the surface of the mold comprising a series of pillars. The basis for the mold is created by sputter-coating a layer of gold film onto the surface of a PTFE cylinder. The pillars are then formed by selectively photoetching the sputter-coated gold film with the aid of a masked photoresist.

SUMMARY OF THE INVENTION

The present invention relates to porous expanded polytetrafluoroethylene (PTFE) material having a microstructure of nodes interconnected by fibrils and further having at least a substantial portion of one surface that is highly hydrophobic as indicated by having a water droplet roll-off angle of less than about 10 degrees. Water droplet roll-off angles for previously available porous expanded PTFE surfaces have been greater than about 12 degrees and are typically greater than about 20 degrees. Porous expanded PTFE surfaces having water droplet roll-off angles of less than about 10 degrees have heretofore been unknown. Some porous expanded PTFE surfaces modified according to the present invention have achieved roll-off angles as low as about 2 degrees.

The present invention may be practiced with porous expanded materials that are very thin, for example, membranes or films of thicknesses as little as about 5 microns.

By a substantial portion of one surface is meant that enough of the one surface has been modified to have an effect on the intended performance of the material, where the intended performance may, for example, involve improved bondability, increased hydrophobicity, improved resistance to the penetration of a fluid through the material or improved filtration ability.

The hydrophilicity or hydrophobicity of any surface is most commonly determined by measurements of the advancing and receding contact angles of distilled water droplets placed onto the horizontal surface in question. However, for purposes of the present invention, water droplet roll-off angle measurements have been found to be the preferred method for measuring high degrees of hydrophobicity. This will be further discussed below.

It has been found that lengthy exposure to radio frequency (rf) etching gas plasmas increases the hydrophobicity of porous expanded PTFE surfaces. This treatment of such a surface by rf gas plasma with most etching gases initially results in increased hydrophilicity. This behavior is known and is in common with the treatment of non-porous PTFE surfaces. This increased hydrophilicity is generally explained in terms of chemical changes in the surface composition. Continued gas plasma treatment results in the achievement of a peak value of hydrophilicity, still the same behavior as non-porous PTFE. Under further treatment, non-porous PTFE remained more hydrophilic than prior to treatment. Porous expanded PTFE, however, after achieving a peak value of hydrophilicity, became increasingly hydrophobic with further treatment and finally approached a maximum level of hydrophobicity that substantially exceeded the degree of hydrophobicity possessed by the unmodified precursor porous expanded PTFE surface. This near-maximum level of hydrophobicity is indicated by a water droplet roll-off angle of less than about 10 degrees and will subsequently be described herein as "highly hydrophobic." It may require more than an hour of treatment time to achieve. The treatment time will depend primarily on the type of plasma etching gas used and on the amount of rf power applied. The gas pressure within the treatment chamber is also a factor.

While only rf gas plasma discharge has been used as the energy source to create the modified surface of the present invention, it is believed that other energy sources such as microwave gas plasma discharge may also be suitable. Other possible energy sources include x-rays, laser beams and ion beams. Lengthy treatment times or high energy levels may be required.

While many reactive gases have been found to be capable of increasing the hydrophobicity of a porous expanded PTFE surface, only some of the reactive gases examined were capable of making the surface highly hydrophobic as indicated by a water droplet roll-off angle of less than about ten degrees.

The minimum treatment time necessary to produce this highly hydrophobic surface results in a surface appearance that is substantially indistinguishable from the surface of the untreated precursor porous expanded PTFE material when both are viewed microscopically. Continued treatment beyond the point of initial highly hydrophobic behavior results in a surface appearance containing broken fibrils, that is, fibrils no longer having both ends connected to adjacent nodes. Still further treatment produces a surface from which the interconnecting fibrils have been removed entirely leaving the portions of the nodes closest to that surface in a freestanding condition, that is, no longer interconnected by fibrils but rather having open valleys disposed between these freestanding node portions. Although the surface morphology undergoes these significant changes as indicated first by the appearance of broken fibrils and subsequently by the complete removal of fibrils, the high degree of hydrophobicity attained prior to the appearance of broken fibrils shows little if any further increase as indicated by water droplet roll-off angle measurements. The material below this modified surface, as evidenced by microscopic views of cross sections of the modified material, appears as conventional, unmodified porous expanded PTFE having a microstructure of nodes interconnected by fibrils.

Surface modified porous expanded PTFE material, having a microstructure of nodes interconnected by fibrils and further having a substantial portion of at least one surface comprised of freestanding node portions with open valleys disposed between the freestanding node portions, is also within the scope of the present invention. This surface may or may not be highly hydrophobic depending primarily on the type of reactive gas plasma used for treatment.

The manufacture of porous expanded PTFE, the precursor material from which the present invention is made, is taught by U.S. Pat. Nos. 3,953,566 and 4,187,390. These patents are herein incorporated by reference.

Porous expanded PTFE having a surface according to the present invention has many applications. For example, it may be possible to make waterproof breathable fabrics of increased performance from the inventive material. The surface modified porous expanded PTFE material may also prove to be a more effective filtration material in certain applications because of its increased hydrophobicity. The modified material surface may also possess enhanced bondability in comparison to unmodified precursor material. It is expected that a modified surface having increased hydrophobicity may improve the flotation characteristics of fly fishing lines having an outer surface of porous expanded PTFE. Wire insulations having an outer surface of porous expanded PTFE may also benefit from the modified surface of the present invention.

Porous expanded PTFE has a long history of use as an implantable material. Various implantable applications of porous expanded PTFE in humans have included vascular grafts, cardiovascular patches for the repair of blood vessels, patches for hernia repair, patches to separate adjacent tissues to prevent tissue adhesions, prosthetic ligaments, sutures, and dental implants for guided tissue regeneration. These products have been commercially available for some time and are consequently quite well known. It is anticipated that many of these previous applications of porous expanded PTFE as an implantable material may be improved by the surface modification methods described herein. Various new implantable applications may also be possible.

The luminal surface of a porous expanded PTFE vascular graft modified to comprise a series of freestanding nodes may have improved blood contact properties because of the effective reduction in the amount of surface area when blood first contacts that surface. For applications involving contact with soft tissues where tissue ingrowth into the void spaces is desirable, the rate or quantity of tissue ingrowth may be improved by the use of a porous expanded PTFE material having a surface of freestanding nodes from which the fibrils have been removed. These tissue ingrowth characteristics are anticipated to be useful for, for example, the outer surface of a breast prosthesis. This application takes advantage of the biocompatibility of the porous expanded PTFE material while the freestanding nodes of the modified outer surface are expected to reduce the phenomena of capsular contraction. For this application, the implantable porous expanded PTFE material can be adhered to the outer surface of a conventional flexible silicone container, typically filled with, for example, a saline solution.

A suture of cylindrical shape having a round cross section and made of porous expanded PTFE having an outer surface modified by removal of fibrils from the outer surface is expected to offer enhanced knot retention.

DETAILED DESCRIPTION OF THE INVENTION

All work described herein was done using a model B12 plasma unit from Advanced Plasma Systems, Inc., St. Petersburg, Fla. Typical surface treatment times ranged from about ten minutes up to as long as about two hours per sample, however, reduced times may be possible with the use of higher rf power. The preferred plasma gas has been NF$_3$ (Air Products, Allentown, Pa.), however, similar results have been achieved with air, argon, oxygen, ammonia and Polyetch™ (Matheson Gas Products, Inc., Utica, Calif.).

Suitable gases are those capable of producing etching or ablation of the PTFE surface. Polymerizing gases, that is gases producing a surface coating of another material, are not suitable. All surface treatments were done at a frequency of 13.56 MHz, chamber pressure of 0.300 torr and 300 watts power unless noted otherwise.

2.5×7.5×0.020 centimeter samples of porous expanded PTFE GORE-TEX Soft Tissue Patch material (W. L. Gore and Associates, Inc. Elkton, Md.) were cut and placed into a special holder that gripped the edges of the sample while leaving the surfaces of the sample exposed. The holder with samples was placed inside the treatment chamber of the B-12 series plasma unit. The square aluminum chamber was of 30.5 centimeters per side having a grounded aluminum electrode in the form of a 23 centimeter per side, square, flat, perforated plate placed vertically in the middle of the chamber and two powered aluminum electrodes of the same size and shape placed vertically on each side of the grounded electrode with their surfaces parallel to the surface of the grounded electrode. The spacing between electrodes was approximately 6.5 centimeters. The samples were suspended vertically between the electrodes with the surfaces to be treated facing a powered electrode.

The chamber was evacuated to 0.020 torr pressure and the desired plasma gas was allowed to flow freely through the chamber for 5 to 10 minutes. The pressure was adjusted to 0.300 torr using a flowmeter mounted on the inlet side of the chamber. After the pressure stabilized at 0.300 torr a plasma was ignited at a 300 watt power level and maintained at these conditions during the treatment. Treatment times used were 1, 2, 3, 4, 5, 10, 15, 20, 30, 60 and 120 minutes. A new set of samples was used for each treatment time.

Hydrophobicity measurements were made by measuring the water droplet roll-off angle for each treated sample. At least 12 measurements of water droplet roll-off angle were taken on each sample to establish a mean value for the sample. The 12 water droplets were placed on 12 different sites on the sample surface. Readings of the roll-off angle were recorded at the moment when the droplet began to roll. The average volume of a water droplet was 0.04 cm$^3$.

It is believed that the increased hydrophobicity resulting from rf gas plasma treatment is due to fibrils, originally lying in or very close to the level of the upper node surfaces, first being depressed or lowered slightly below that level. Continued treatment next results in breakage of some of these fibrils and finally in their complete removal from the level of the upper node surfaces and downward to some depth below that level. Still further continued treatment increases the depth of fibril removal. Prolonged treatment results in microscopically visible node ablation that appears to ultimately limit the maximum achievable depth of fibril removal. This can be explained by the assumed slower rate of fibril removal at this depth. This maximum achievable depth appears to be a function of the microstructure of the precursor material as well as of the gas plasma application parameters.

The magnified appearance of the surface from which the fibrils have been entirely removed is thus the appearance of the portions of the nodes closest to the surface in a freestanding condition, that is, no longer having fibrils interconnecting these freestanding node portions but rather having open valleys disposed between these freestanding node portions. The valley floors, that is, the bottom of the valleys, are generally comprised of fibrils. Because the surface of the microstructure has been modified only to the extent of removal of the fibrils therefrom, no apparent difference to the surface is visible to the naked eye. Magnification of the surface is required in order to make the result of the modification visible. Surfaces modified as taught by the macrostructural techniques of U.S. Pat. Nos. 4,208,745, 4,332,035 and 4,647,416 are thus not within the scope of the present invention.

The best mode of practicing the present invention is believed to be the use of rf gas plasma discharge with $NF_3$ gas to modify a porous expanded PTFE surface for a long enough time to create a surface comprised of freestanding node portions having open valleys disposed between the freestanding node portions. $NF_3$ is preferred because it is readily available, is relatively economical, requires less etching time than other gases examined heretofore and produces a highly hydrophobic surface.

The increased hydrophobicity of the plasma treated porous expanded PTFE surfaces, as indicated by either higher water droplet contact angles or by lower water droplet roll-off angles, is believed to be a result of the water droplet resting on a reduced surface area of the modified material. It is believed that plasma treatment initially causes depression of the fibrils from the level of the upper node surfaces, followed by breakage of those fibrils and finally followed by the entire removal of fibrils from the surface. Thus it appears that when hydrophobicity of the surface modified porous expanded PTFE is measured by the use of a water droplet that the droplet is only in contact with the upper node surfaces and that very few, if any, of the fibrils closest to the surface are in contact with the water droplet. This is in contrast to the unmodified material wherein both the upper node surfaces and the fibrils closest to the material surface are believed to be in contact with the water droplet.

The hydrophilicity or hydrophobicity of any surface is most commonly determined by measurements of the advancing and receding contact angles of distilled water droplets placed onto the horizontal surface in question as taught by ASTM D 724-45. Material surfaces having water droplet contact angles less than 90 degrees are considered to be hydrophilic while contact angles greater than 90 degrees indicate hydrophobicity. A typical porous expanded PTFE surface that has not been modified according to the present invention has a water droplet contact angle of about 120 to 160 degrees while such surfaces that have been modified as taught herein have contact angles generally greater than about 170 degrees. Apparently due to the increased roughness of the modified surfaces, it is difficult to achieve consistent water droplet contact angle measurements because of increased hysteresis between the advancing and receding contact angles. Furthermore, as the contact angle approaches 180 degrees, the angle becomes more difficult to project and measure accurately due to irregularities of the surface. Water droplet roll-off angle measurements have been found to be the preferred method of measuring the hydrophobicity of rough surfaces and in particular surfaces modified by the present invention. Water droplet roll-off angle measurements are more easily made and the results appear to be more consistent than contact angle measurements for such surfaces. This has been confirmed by Y. Iriyama et al., Plasma Surface Treatment on Nylon Fabrics by Fluorocarbon Compounds, Journal of Applied Polymer Science 1990 39;249–264.

Figure 1:
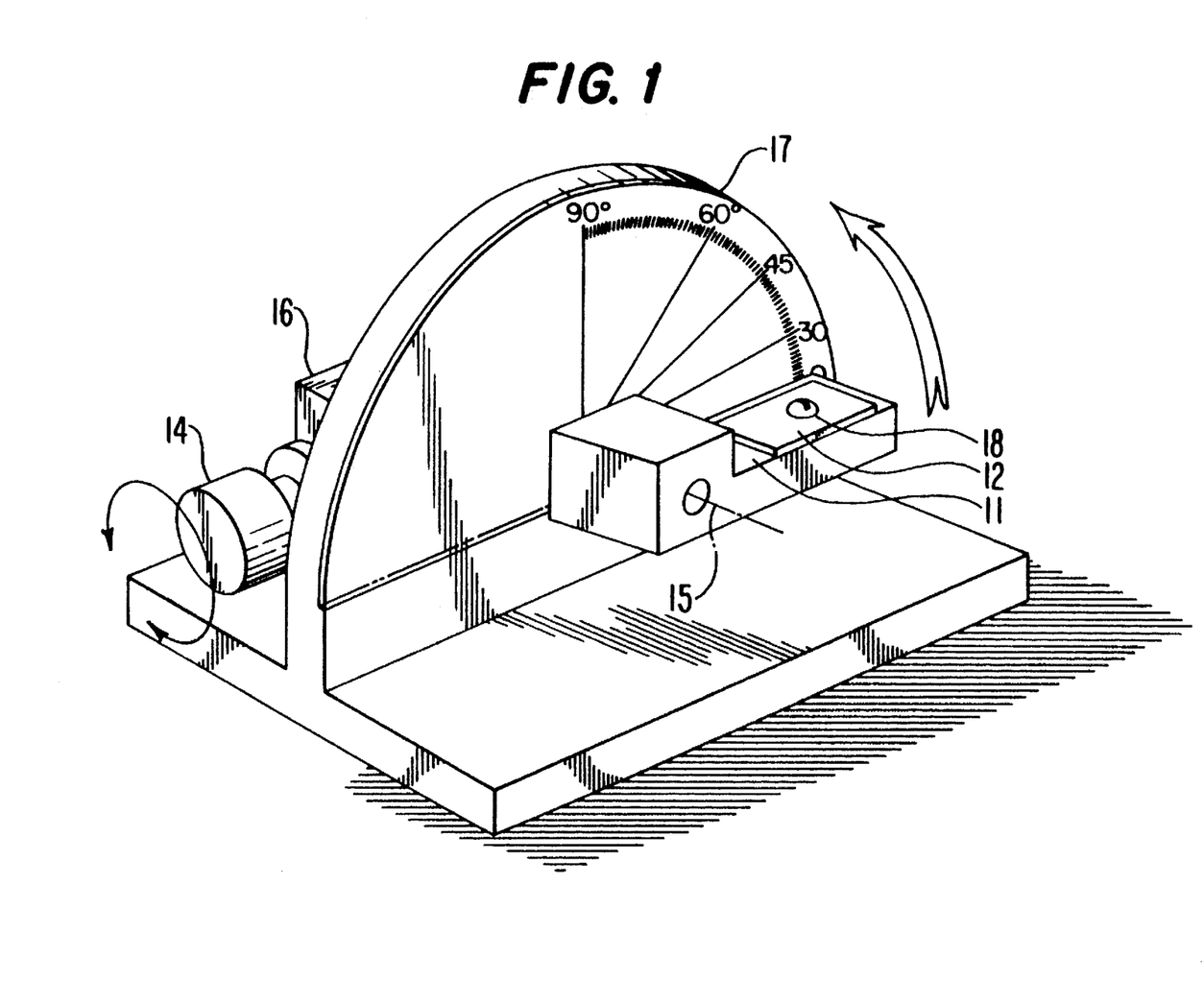
FIG. 1 is a drawing of a device used for measuring water droplet roll-off angles for the material samples of this invention.

FIG. 1 shows the apparatus used to measure water droplet roll-off angles for hydrophobicity measurements. A sample 12 of material to be measured is placed onto the plane surface 11 so that the sample 12 is uniformly in contact with the plane surface 11. An adjustment knob 14 connected to a right-angle gearhead 16 is used to rotate the plane surface 11 about axis 15. Axis 15 is horizontally oriented, that is, perpendicular to the direction of the force of gravity. A protractor 17 is set up adjacent and perpendicular to the plane surface 11 with its center in line with axis 15, allowing easy measurement of the angle between the plane surface 11 and the horizontal. In use, the plane surface 11 is placed into a horizontal position and a material sample 12 is placed onto the plane surface 11 so that it uniformly contacts the plane surface 11. A droplet of distilled water 18 is placed onto the surface of the material sample 12. The adjustment knob 14 is turned by hand to cause slow rotation of the plane surface 11 about axis 15 at an angular velocity of approximately one degree per second. When the water droplet 18 begins to roll off of the surface of the material sample 12, the roll-off angle is measured from the protractor as the tilt angle of the plane surface 11. Multiple individual water droplets may be placed onto a single sample if the sample is of adequate area. In measurements described herein, the data represent the average roll-off angle of at least 12 water droplets.

Water droplet roll-off angles for unmodified porous expanded PTFE surfaces are typically greater than about 20 degrees while water droplet roll-off angles of porous expanded PTFE surfaces treated by the method of the present invention are typically less than about 10 degrees. The lowest water droplet roll-off angle of known porous expanded PTFE surfaces has been that of the luminal surface of GORE-TEX Vascular Graft material (W. L. Gore and Associates, Inc., Elkton, Md.), which typically measures about 12 degrees.

Figure 2:
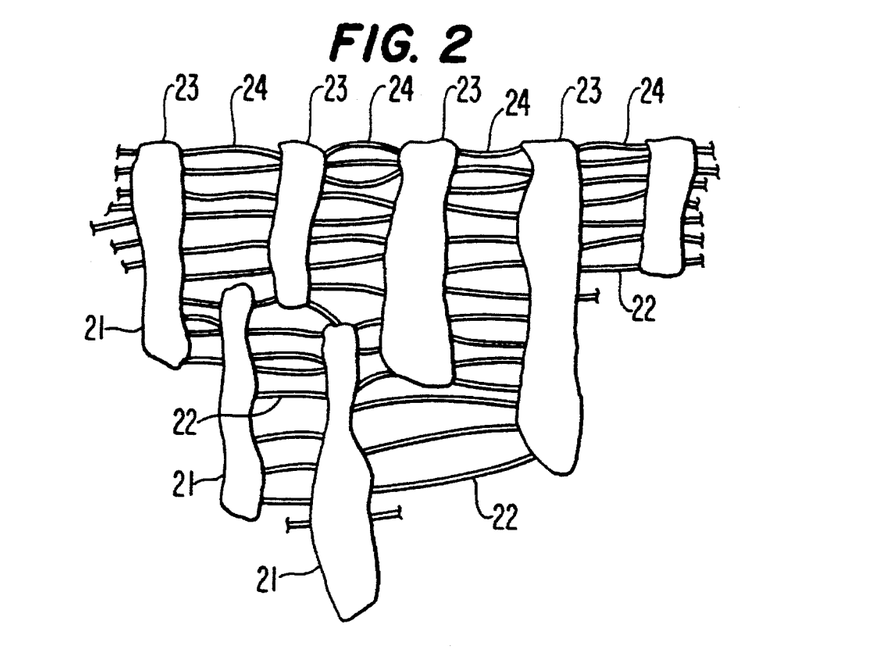
FIG. 2 shows a pictorial representation of an enlarged cross sectional view of a precursor porous expanded PTFE material prior to plasma treatment.
Figure 2A:
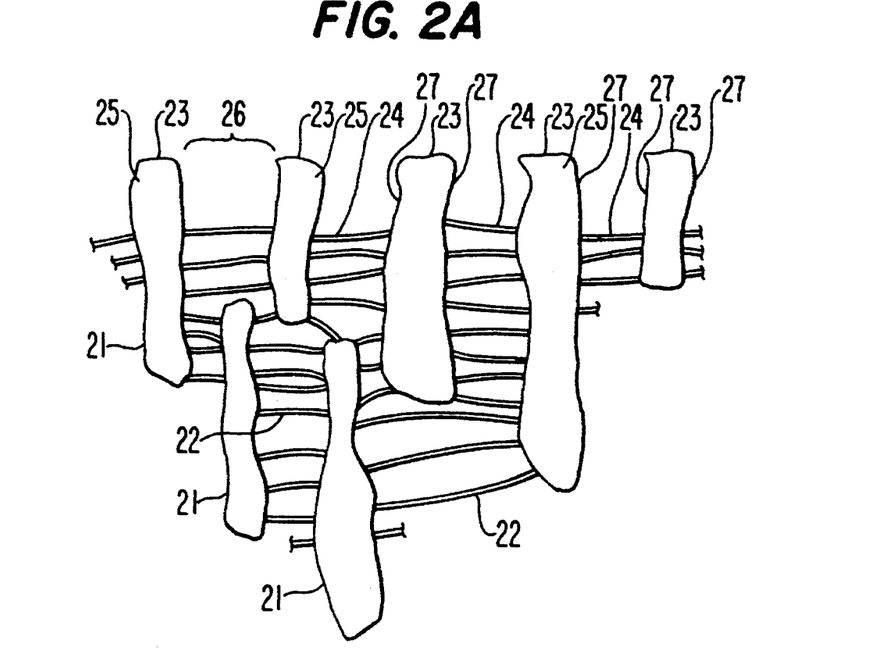
FIG. 2A shows a pictorial representation of an enlarged cross sectional view of the material of FIG. 2 after rf gas plasma treatment with a reactive etching gas.

FIG. 2 is a pictorial representation of a cross sectional view of a precursor porous expanded PTFE material prior to any modification. This figure shows the microstructure of nodes 21 interconnected by fibrils 22. The surface of the material is comprised of upper node surfaces 23 and fibrils 24 closest to the surface. FIG. 2A is a pictorial representation of a cross sectional view of the same material after rf gas plasma treatment to modify the surface to the extent of removing fibrils from the surface. This figure shows freestanding node portions 25 with open valleys 26 disposed between the freestanding node portions 25. The modified surface of the material is comprised of the freestanding node portions 25 and fibrils 24 closest to the surface. The fibrils 24 closest to the surface now form the floors of the open valleys 26. The microscopically visible freestanding node portions 25 are comprised of upper node surfaces 23 and exposed vertical node surfaces 27 no longer having interconnecting fibrils attached.

Figure 3:
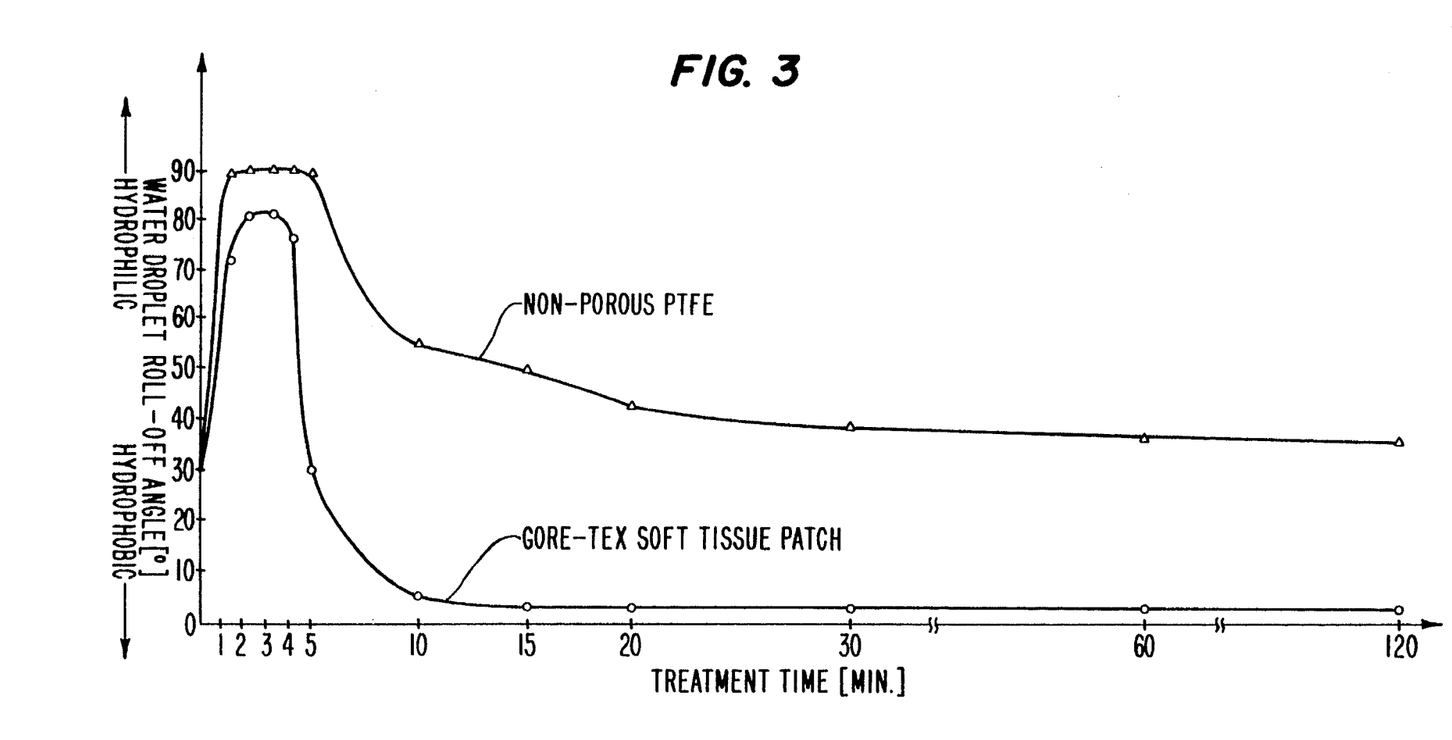
FIG. 3 shows a graph of the change in water droplet roll-off angles of both non-porous PTFE and porous expanded PTFE surfaces as a function of different treatment times by rf glow discharge gas plasma using nitrogen trifluoride (hereinafter $NF_3$) gas.

FIG. 3 shows a graph of the change in water droplet roll-off angle of a porous expanded PTFE material surface in comparison to a non-porous PTFE surface when samples of both materials were treated with rf gas plasma for varying amounts of time. Water droplet roll-off angle is plotted on the vertical axis against treatment time on the horizontal axis. The plasma gas used was $NF_3$. The porous expanded PTFE material was GORE-TEX Soft Tissue Patch.

As shown by the graph of FIG. 3, the porous expanded PTFE surface became increasingly wettable or hydrophilic as the surface was initially treated by gas plasma discharge. A maximum water droplet roll-off angle of about 80 degrees was achieved after about two minutes of treatment. Further treatment, however, resulted in a decrease in hydrophilicity. As treatment continued, the porous expanded PTFE surface surpassed the degree of hydrophobicity it possessed prior to any treatment and became increasingly hydrophobic until a maximum degree of hydrophobicity was approached after about ten minutes of treatment, as indicated by a water droplet roll-off angle of about 5 degrees. Two hours of treatment resulted in no further significant increase in hydrophobicity.

The non-porous PTFE surface also described in FIG. 3 showed similar behavior in that initial gas plasma treatment made the surface more hydrophilic. Continued treatment resulted in a decrease in hydrophilicity until a water droplet roll-off angle of slightly less than about 40 degrees was ultimately achieved and beyond which no further change was seen. Thus, unlike the porous expanded PTFE surface, the treated non-porous PTFE surface remained more hydrophilic than the untreated precursor material.

Figure 4:
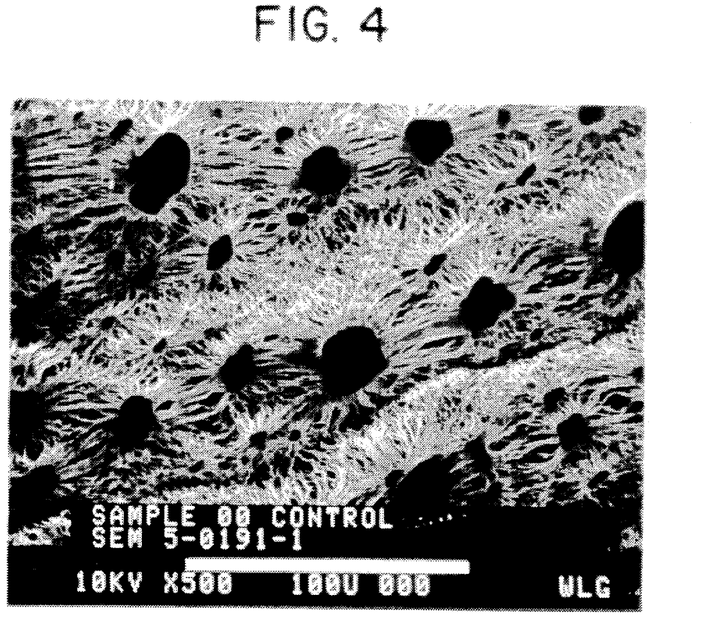
FIG. 4 shows a scanning electron photomicrograph (×500) of the surface of a porous expanded PTFE material (GORE-TEX® Soft Tissue Patch) prior to rf gas plasma treatment.
Figure 4A:
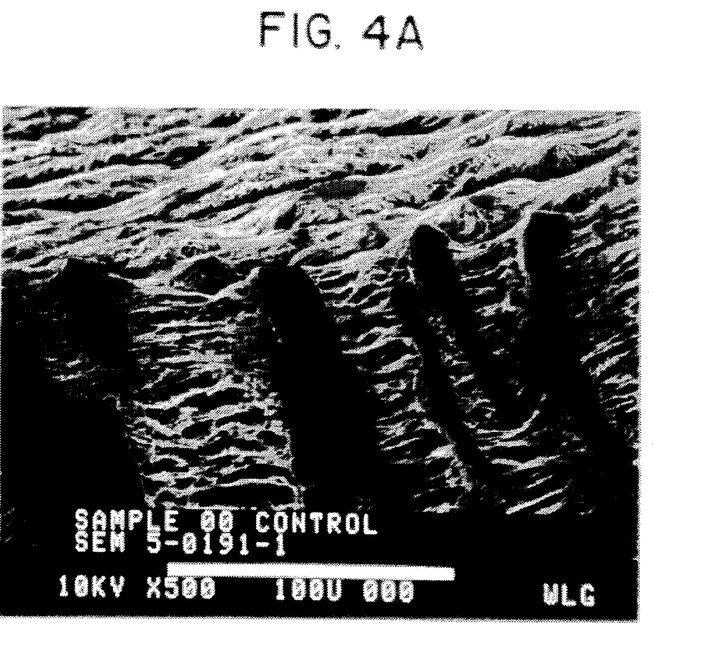
FIG. 4A shows a scanning electron photomicrograph (×500) of a perspective cross sectional view of the material of FIG. 4 prior to rf gas plasma treatment.
Figure 5:
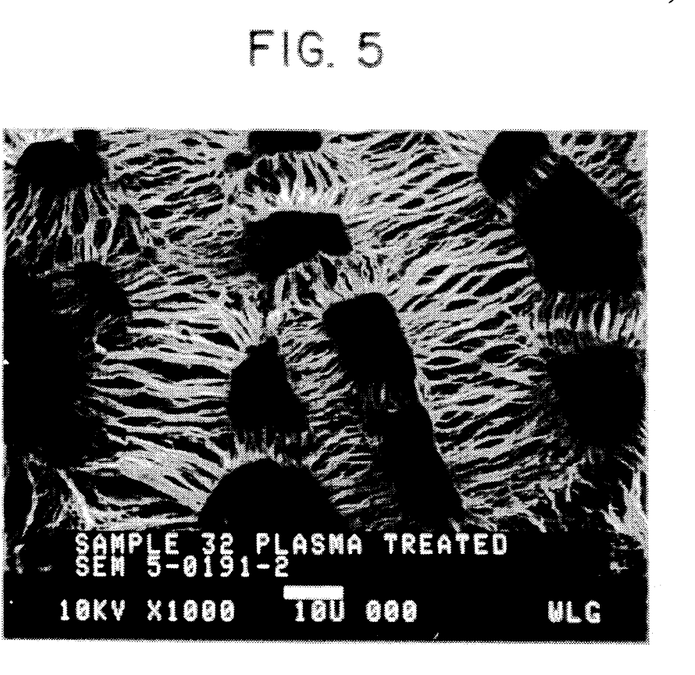
FIG. 5 shows a scanning electron photomicrograph (×1000) of the surface of the same material as shown by FIG. 4 after 2 minutes of rf gas plasma treatment with $NF_3$ gas to make the surface hydrophilic.
Figure 5A:
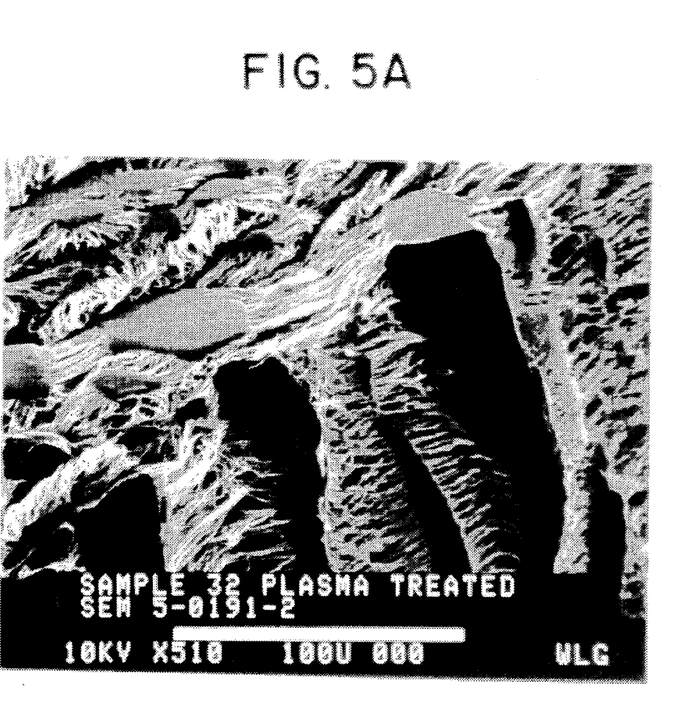
FIG. 5A shows a scanning electron photomicrograph (×500) of a perspective cross sectional view of the material of FIG. 4A after 2 minutes of rf gas plasma treatment with $NF_3$ gas to make the surface hydrophilic.
Figure 6:
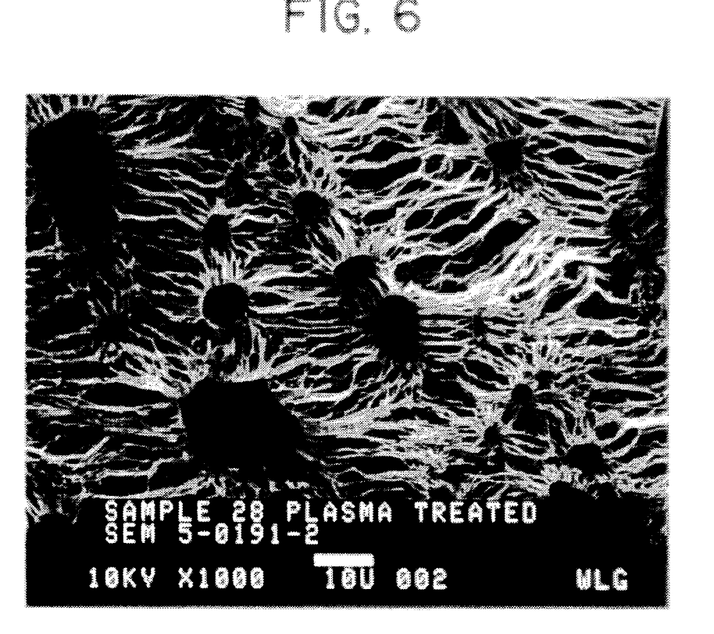
FIG. 6 shows a scanning electron photomicrograph (×1000) of the surface of the same material as shown by FIG. 4 after 10 minutes of rf gas plasma treatment with $NF_3$ gas to make the surface highly hydrophobic.
Figure 6A:
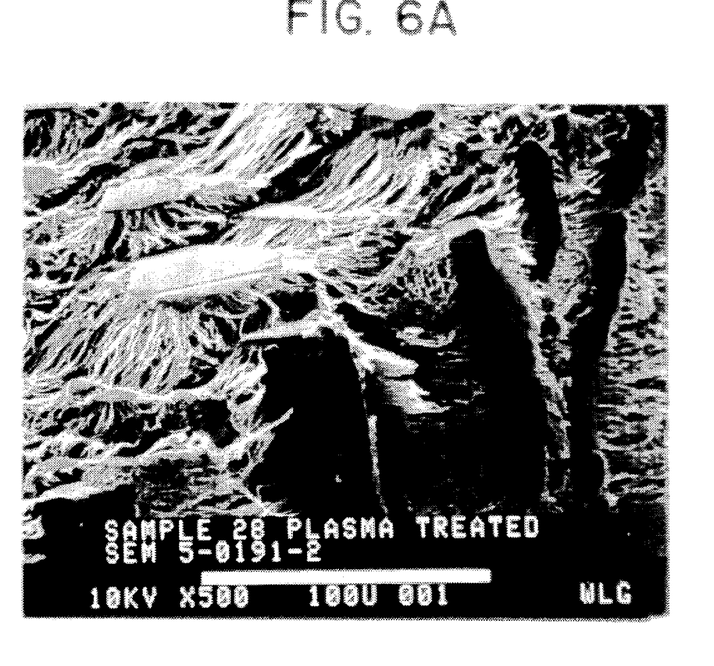
FIG. 6A shows a scanning electron photomicrograph (×500) of a perspective cross sectional view of the same material as shown by FIG. 4A after 10 minutes of rf gas plasma treatment with $NF_3$ gas to make the surface highly hydrophobic.

FIG. 4 shows a scanning electron photomicrograph (×500) of the surface of the untreated precursor porous expanded PTFE material (GORE-TEX Soft Tissue Patch) which had a water droplet roll-off angle of 29 degrees as indicated by the graph of FIG. 3. FIG. 4A shows a photomicrograph (×500) of a perspective cross section of the same untreated precursor material. The foreground material in the lower portion of the photomicrograph is the cross sectional view while the material shown in the upper part of the photomicrograph is the surface of the material shown in perspective. This presentation is typical of all perspective, cross sections shown herein. FIGS. 5 (×1000) and 5A (×500) show surface and perspective cross sectional views respectively of the same material that has been gas plasma treated for 2 minutes as described by the graph of FIG. 3. While the plasma treated surface shown by FIGS. 5 and 5A is much more hydrophilic than the unmodified surface shown by FIGS. 4 and 4A, the magnified treated and untreated surfaces do not appear to be visually distinguishable. FIGS. 6 (×1000) and 6A (×500) show surface and perspective cross sectional views respectively of the same material that has been gas plasma treated for 10 minutes as described by the graph of FIG. 3. Although the plasma treated surface of FIGS. 6 and 6A was much more hydrophobic than the unmodified surface of FIGS. 4 and 4A, the magnified treated and untreated surfaces appear to be visually indistinguishable. While it is not visually apparent under microscopy, it is believed that the highly hydrophobic behavior of the 10 minute $NF_3$ plasma treated sample shown by FIGS. 6 and 6A is the result of the fibrils nearest the material surface being lowered or depressed downward away from the material surface.

Figure 7:
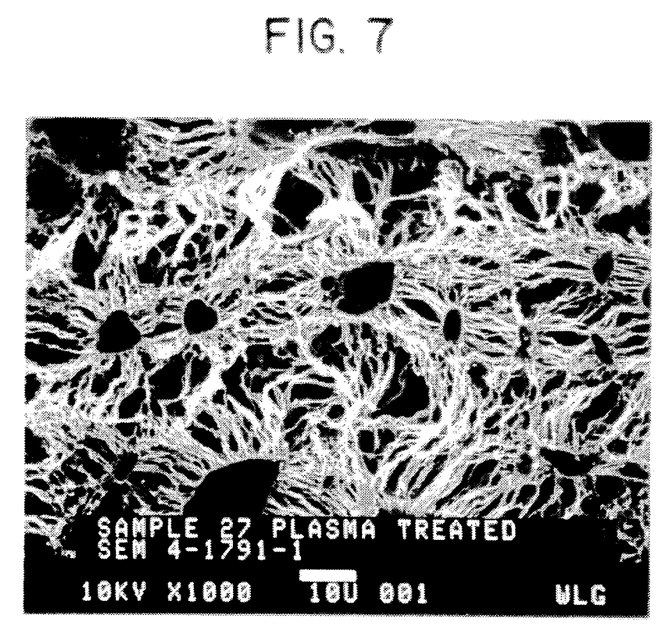
FIG. 7 shows a scanning electron photomicrograph (×1000) of the surface of the same material as shown by FIG. 4 after 15 minutes of rf gas plasma treatment with $NF_3$ gas resulting in broken fibrils at the material surface.
Figure 7A:
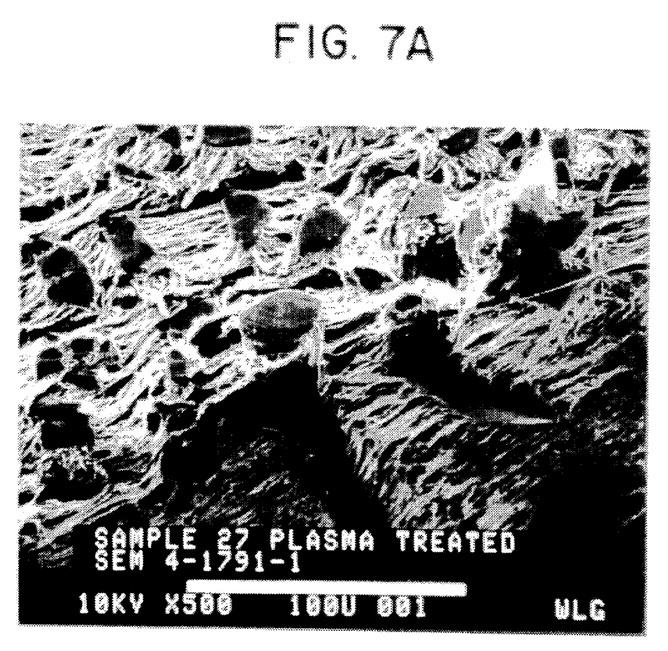
FIG. 7A shows a scanning electron photomicrograph (×500) of a perspective cross sectional view of the same treated material as shown by FIG. 4A after 15 minutes of rf gas plasma treatment with NF$_3$ gas resulting in broken fibrils at the material surface.

FIGS. 7 (×1000) and 7A (×500) are photomicrographs of the same porous expanded PTFE surface and perspective cross section that has been $NF_3$ gas plasma treated, this time for 15 minutes, as described by the graph of FIG. 3. The broken fibrils of the plasma treated surface of FIGS. 7 and 7A are apparent. FIGS. 7 and 7A show also the upper node surfaces to be somewhat elevated above the adjacent interconnecting fibrils as a probable result of the removal by etching of some surface fibrils. The photomicrograph of FIG. 7 suggests subjectively that about 20 percent of the fibrils comprising the surface have been broken. Typical precursor materials do not appear to contain more than about 1 percent of broken fibrils out of the total number of fibrils visible at their surface. It is believed that a surface containing more than about 5 percent visible broken fibrils within the surface is unique to the highly hydrophobic material of the present invention.

Figure 8:
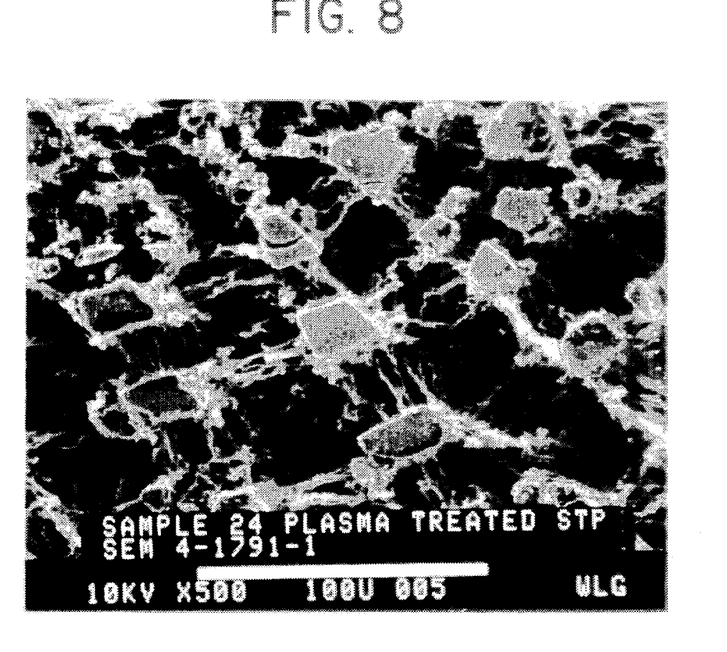
FIG. 8 shows a scanning electron photomicrograph (×500) of the surface of the same material as shown by FIG. 4 after 60 minutes of rf gas plasma treatment with NF$_3$ gas resulting in removal of the fibrils from the material surface leaving the surface comprised of a series of freestanding node portions with open valleys disposed between the freestanding node portions.
Figure 8A:
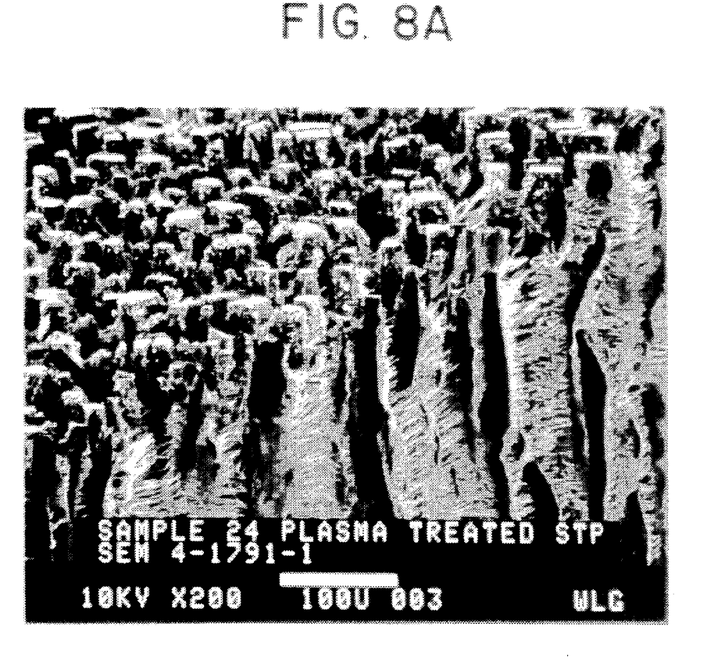
FIG. 8A shows a scanning electron photomicrograph (×200) of a perspective cross sectional view of the same material as shown by FIG. 4A after 60 minutes of rf gas plasma treatment with NF$_3$ gas resulting in removal of the fibrils from the material surface leaving the surface comprised of a series of freestanding node portions with open valleys disposed between the freestanding node portions.
Figure 9:
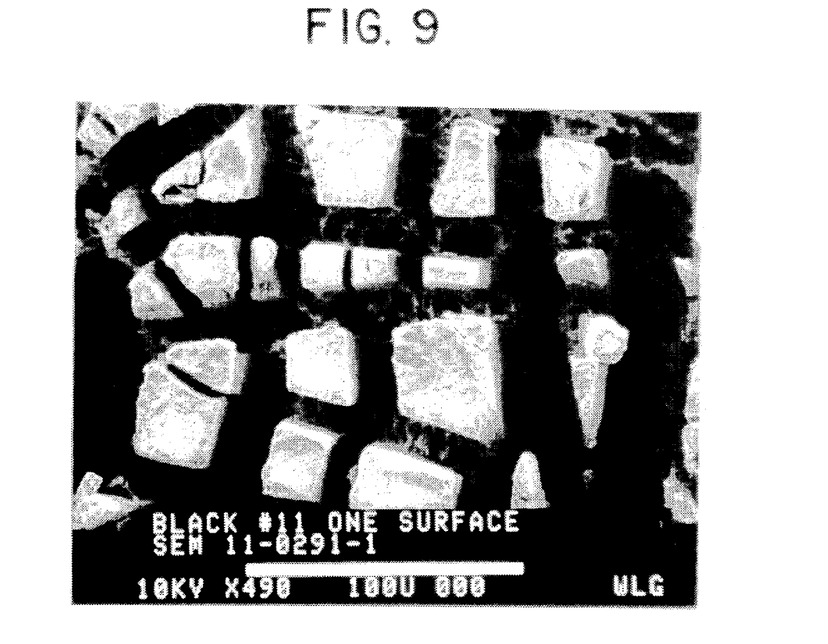
FIG. 9 shows a scanning electron photomicrograph (×500) of a surface view of the same material as shown by FIG. 4 after 120 minutes of rf gas plasma treatment with air resulting in removal of the fibrils from the material surface leaving the surface comprised of a series of freestanding node portions with open valleys disposed between the freestanding node portions.
Figure 9A:
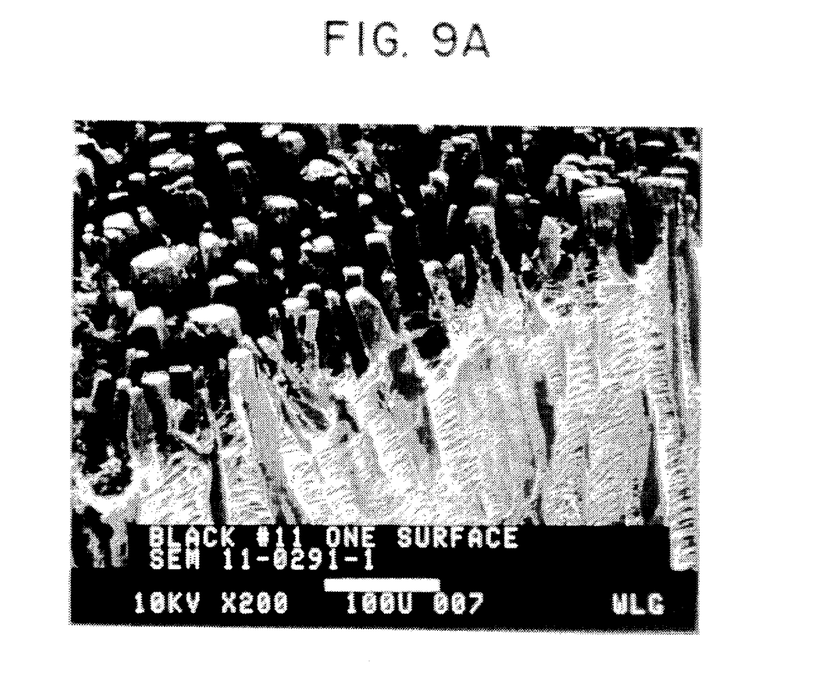
FIG. 9A shows a scanning electron photomicrograph (×200) of a perspective cross sectional view of the same material as shown by FIG. 4A after 120 minutes of rf gas plasma treatment with air resulting in removal of the fibrils from the material surface leaving the surface comprised of a series of freestanding node portions with open valleys disposed between the freestanding node portions.

FIGS. 8 (×500) and 8A (×200) show a surface and perspective cross sectional view of the same material that has been $NF_3$ gas plasma treated even longer, this time for 60 minutes as described by the graph of FIG. 3. FIGS. 9 (×500) and 9A (×200) show a surface and perspective cross sections of the same material that has been exposed to gas plasma treatment with air for a period of 120 minutes. These figures all show a surface from which the fibrils have been entirely removed from between the node portions closest to the surface so that the surface morphology is now comprised of freestanding node portions having open valleys disposed between the freestanding node portions. The valley floors are comprised of fibrils closest to the surface. As with the sample surface shown by FIGS. 7 and 7A, the surfaces of FIGS. 8 and 8A are highly hydrophobic but only very slightly more than the sample surface shown by FIG. 6. The comparative water droplet roll-off angle data is shown by the graph of FIG. 3. The surfaces shown by FIGS. 9 and 9A are not highly hydrophobic, having a water droplet roll-off angle of about 18 degrees.

Figure 10:
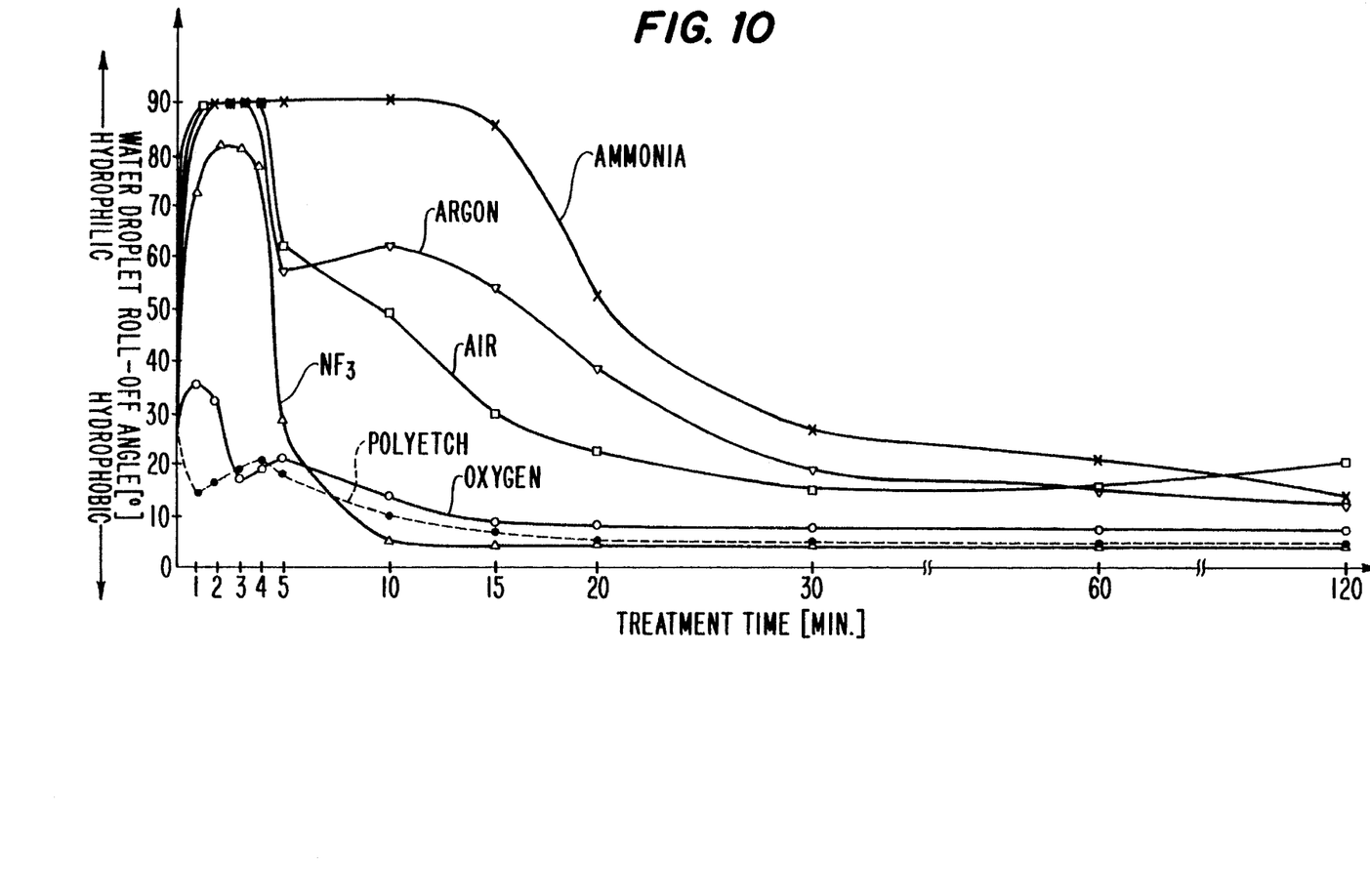
FIG. 10 shows a graph of the change in water droplet roll-off angle of a porous expanded PTFE material (GORE-TEX Soft Tissue Patch) as a function of different treatment times by glow discharge plasma for different gases.

FIG. 10 is a graph of water droplet roll-off angle versus treatment time for surface treatment of porous expanded PTFE (GORE-TEX Soft Tissue Patch) for different types of gases. Air, $NF_3$, argon, oxygen, ammonia and Polyetch are shown. All treatments shown ultimately produced increased hydrophobicity and a surface comprised of freestanding node portions having open valleys disposed between the freestanding node portions. However, some gases did not produce highly hydrophobic surfaces as indicated by those surfaces having water droplet roll-off angles greater than about ten degrees. Very little difference was seen to result from the use of different gases as long as the chosen gas was a reactive etching gas. The primary difference seen between the different gases shown by FIG. 10 was in the length of treatment time required to produce the surface comprised of freestanding node portions.

Figure 11:
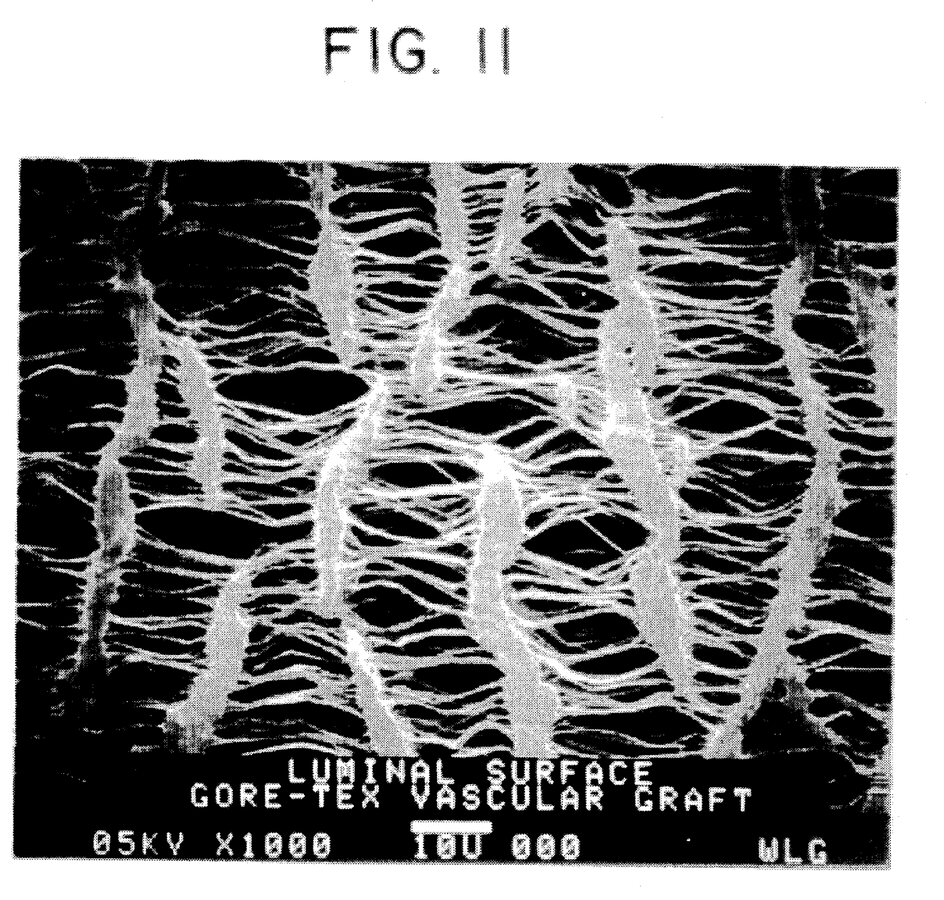
FIG. 11 shows a scanning electron photomicrograph (×1000) of the luminal surface of an alternative porous expanded PTFE material (20 mm diameter GORE-TEX Vascular Graft) prior to rf gas plasma treatment.

FIG. 11 shows a scanning electron photomicrograph (×1000) of an alternative porous expanded PTFE surface prior to any surface treatment. The material shown is a commercially available 20 mm GORE-TEX Vascular Graft. The surface shown is the luminal surface of the vascular graft.

Figure 12:
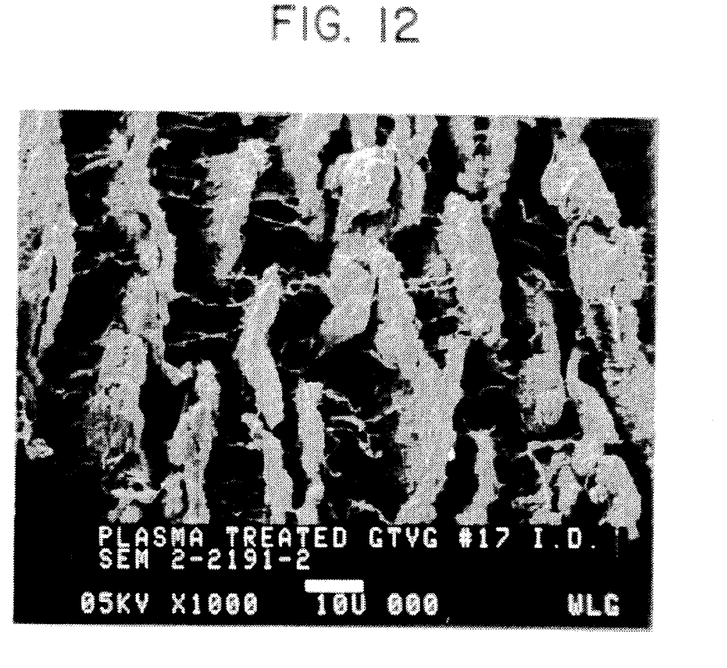
FIG. 12 shows a scanning electron photomicrograph (×1000) of the luminal surface of the same material as shown by FIG. 10 after 30 minutes of rf gas plasma treatment with oxygen resulting in the removal of fibrils from the surface leaving the surface comprised of freestanding node portions having open valleys disposed between the freestanding node portions.
Figure 13:
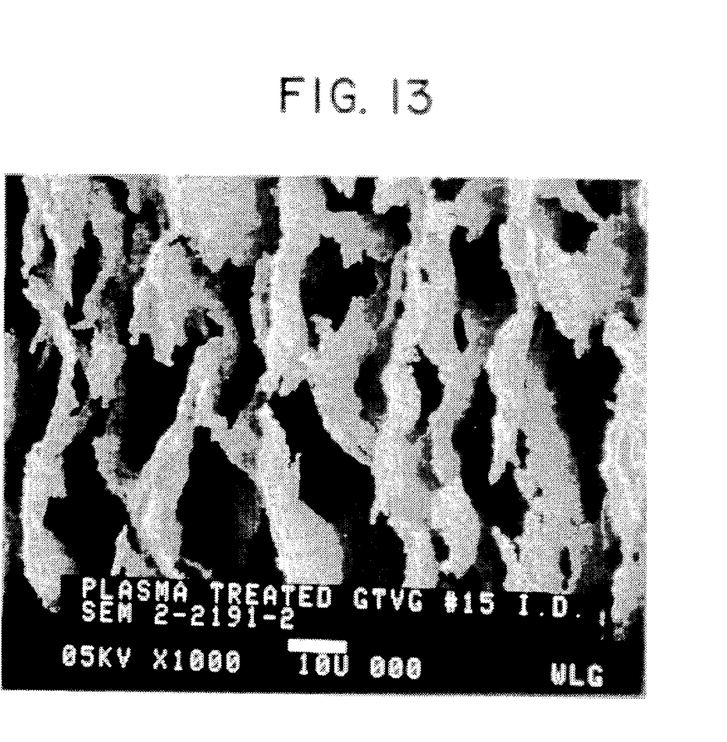
FIG. 13 shows a scanning electron photomicrograph (×1000) of the luminal vascular graft surface of the same material as shown by FIG. 10 after 120 minutes of rf gas plasma treatment with oxygen resulting in the removal of fibrils from the surface leaving the surface comprised of freestanding node portions having open valleys disposed between the freestanding node portions.

FIG. 12 depicts a scanning electron photomicrograph (×1000) of the luminal surface of another sample of the same GORE-TEX Vascular Graft material after lengthy treatment by glow discharge plasma using oxygen as the plasma gas. The treatment time was 30 minutes. The removal of the fibrils that normally interconnect the nodes is apparent. No modification to the nodes appears to take place other than some ablation. FIG. 13 (×1000) shows another sample of the same material surface after having been exposed to the same treatment for 120 minutes.

I claim:

1. An implantable material comprising porous expanded polytetrafluoroethylene having a microstructure comprised of nodes interconnected by fibrils, said porous expanded polytetrafluoroethylene comprising a three dimensional material having at least one surface wherein at least a substantial portion of the at least one surface is comprised of freestanding node portions with open valleys disposed between the freestanding node portions.

2. An implantable material according to claim 1 wherein the porous expanded polytetrafluoroethylene has a water droplet roll-off angle of less than about 10 degrees.

3. An implantable material according to claim 1 wherein the porous expanded polytetrafluoroethylene has a water droplet roll-off angle of less than about 8 degrees.

4. An implantable material according to claim 1 wherein the porous expanded polytetrafluoroethylene has a water droplet roll-off angle of less than about 6 degrees.

5. An implantable material according to claim 1 wherein the porous expanded polytetrafluoroethylene has a water droplet roll-off angle of less than about 4 degrees.

6. An implantable material according to claim 1 wherein the three dimensional material is in the form of a tubular shape having an inner surface and an outer surface and the at least one surface comprises the inner surface of the tubular shape.

7. An implantable material according to claim 6 wherein the tubular shape is a vascular graft.

8. An implantable material according to claim 1 wherein the implantable material comprises the outer surface of a breast prosthesis.

9. An implantable material according to claim 1 wherein the implantable material comprises the outer surface of a breast prosthesis and wherein the porous expanded polytetrafluoroethylene is adhered to the outer surface of a flexible silicone container.

10. An implantable material according to claim 1 wherein the three dimensional material is in the form of a tubular shape having an inner surface and an outer surface and the at least one surface comprises the outer surface of the tubular shape.

11. An implantable material according to claim 10 wherein the tubular shape is a vascular graft.

12. An implantable material according to claim 1 wherein the three dimensional material is in the form of a flat sheet.

13. An implantable material according to claim 12 wherein the flat sheet is an implantable patch.

14. An implantable material according to claim 12 wherein the flat sheet is an implantable membrane.

15. An implantable material according to claim 1 wherein the three dimensional material is in the form of a cylindrical shape having a curved outer surface and the at least one surface comprises the curved outer surface.

16. An implantable material according to claim 15 wherein the cylindrical shape is a suture.

17. A method of modifying a surface of an implantable porous expanded polytetrafluoroethylene material, said implantable porous expanded polytetrafluoroethylene material having a microstructure of nodes interconnected by fibrils, said method comprising exposing the surface to a reactive gas plasma discharge until the fibrils are removed from at least a substantial portion of the surface and the surface is comprised of freestanding node portions with open valleys disposed between the freestanding node portions.

* * * * *